United States Patent [19]

Loescher et al.

[11] Patent Number: 4,990,894
[45] Date of Patent: Feb. 5, 1991

[54] VENTILATOR MONITOR AND ALARM APPARATUS

[75] Inventors: Thomas C. Loescher, Encinitas; Robert O. Rowland, Hemet, both of Calif.

[73] Assignee: Hudson Respiratory Care Inc., Temecula, Calif.

[21] Appl. No.: 430,309

[22] Filed: Nov. 1, 1989

[51] Int. Cl.⁵ .............................................. G08B 23/00
[52] U.S. Cl. .................................. 340/573; 340/626; 128/204.21
[58] Field of Search ...................... 340/573, 626, 611; 128/202.22, 200.24, 204.21, 204.23

[56] References Cited

U.S. PATENT DOCUMENTS

| | | | |
|---|---|---|---|
| 4,300,548 | 11/1981 | Jones | 128/202.22 |
| 4,598,279 | 7/1986 | Howacki et al. | 340/626 |
| 4,803,471 | 2/1989 | Rowland | 340/626 |
| 4,883,051 | 11/1989 | Westenskow et al. | 128/204.21 |

Primary Examiner—Joseph A. Orsino
Assistant Examiner—Geoff Sutcliffe
Attorney, Agent, or Firm—Jerry R. Seiler

[57] ABSTRACT

An improved apparatus for monitoring a respiratory circuit comprises two independent pressure sensing means, a first pressure sensing component having a preset minimum pressure for creating an alarm condition in response to pressure falling below the minimum, and a second pressure sensing component having an adjustable low pressure threshold setting means and for creating an alarm condition if the patient breathing cycle pressure fails to periodically pass through the low threshold pressure. A preferred embodiment includes visual pressure indicating means including a display of the low threshold pressure setting and a display of the patient breathing cycle pressures.

19 Claims, 8 Drawing Sheets

VENTILATOR MONITOR AND ALARM APPARATUS

BACKGROUND OF THE INVENTION

Ventilator monitor and alarm apparatus are used for monitoring a patient or user breathing in a ventilator circuit, and to create an alarm when patient breathing falls below or rises above preselected desired minimum or maximum pressure, respectively. One such device for monitoring patient ventilator circuit breathing and alarming when pressure falls below a preselected minimum is disclosed in U.S. Pat. No. 4,803,471. The apparatus disclosed in that patent also includes an automatic on feature which turns the apparatus on, independent of an on/off switch when the device senses the preselected minimum pressure in the breathing circuit. However, in the aforesaid prior art apparatus, if the therapist, nurse or person operating the device sets the preselected minimum pressure too low, although the unit is turned on by the patient's first breath, it would not alarm where the sensed ventilator pressure is above the preselected minimum, regardless of the patient's breathing cycle pressure. For example, the ventilator circuit tubing may be crimped, occluded or the circuit otherwise malfunctioning, but with a sensed circuit pressure higher than the preselected minimum pressure an alarm condition is prevented from occurring. On the other hand, in such an apparatus, if the preselected minimum is set too high, the device would not be automatically turned on since the automatic on function only operates when the circuit pressure passes through the preselected minimum for the first time.

In yet another ventilator circuit monitoring and alarm apparatus disclosed in U.S. Pat. No. 4,316,182, the automatic on feature is not provided with any adjustment for selecting a desired minimum pressure. Since there is no adjustment of the minimum pressure, although the apparatus monitors the patient's breathing cycle, if the pressure of the patient's first breath is not enough to close a breath detection switch, the unit will not be turned on. In addition, a patient having a very low or shallow breathing pressure cycle might not create an alarm condition.

SUMMARY OF THE INVENTION

The present invention comprises a ventilator circuit monitor and alarm having improved features including an automatic on as well as providing for operator selection and adjustment of the minimum pressure. The apparatus includes two pressure switches for monitoring ventilator circuit pressure, one preset at a first low pressure, and an adjustable low pressure i threshold transducer for monitoring the patient's breathing cycle pressure and for creating an alarm condition if the pressure does not pass through the threshold within a preselected time period. The apparatus includes an adjustable high pressure limit monitoring means for creating an alarm if the breathing pressure exceeds the high limit threshold, and a visual positive pressure breath indicator and bar graph manometer display. These visual displays allow the operator to see the minimum low pressure threshold which has been selected and at the same time observe the patient's breathing cycle on the bar graph manometer display. These as well as other improvements and features of the apparatus of the invention will be evident from the following detailed description.

BRIEF DESCRIPTION OF THE DRAWINGS

FIGS. 6-1, 6-2, 6-3, 7-1, and 7-2 are detailed schematic diagrams of the electronic components of the apparatus of the invention.

DETAILED DESCRIPTION OF THE INVENTION

Figure 1:
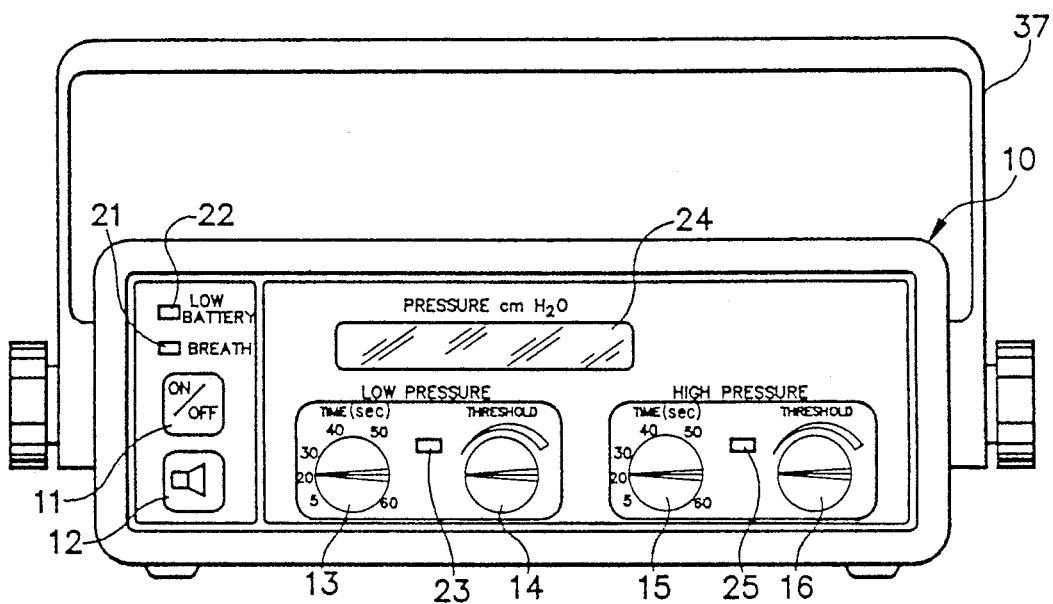
FIG. 1 is a front view of a preferred embodiment of the apparatus of the invention illustrating the switches, pressure and time adjustment components.

Referring to FIG. 1, the apparatus includes a case or housing 10 having a front panel including an on/off switch or button 11, an alarm silence button 12, a low pressure time delay adjustment knob 13, low threshold pressure adjustment knob 14 and low pressure LED 23. The high pressure adjustments and indicator include time delay adjustment knob 15 and high pressure adjustment knob 16 with visual high pressure alarm LED 25. A visual low battery LED indicator 22 and visual pressure breath indicator LED 21 also are provided. The LCD visual displays of the manometer and low pressure threshold set points are in display panel 24 which is further shown in more detail in FIG. 3.

Figure 2:
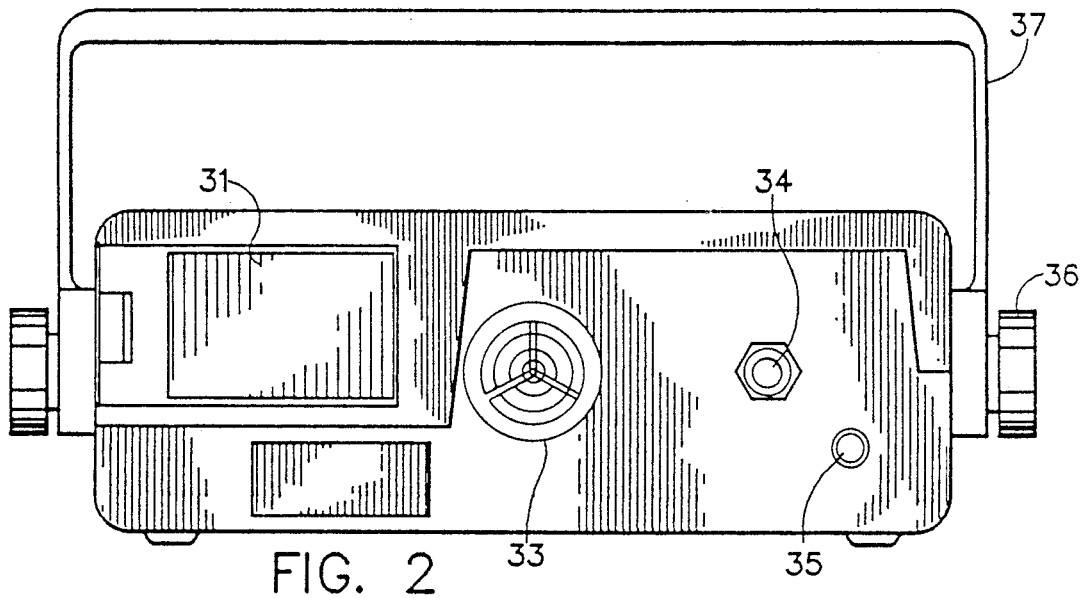
FIG. 2 is a rear view of the apparatus illustrated in FIG. 1.

The features illustrated in FIG. 2 of the rear or back panel of the device include a pressure inlet port 34, an offset adjustment screw 35, audible alarm grill 33, case handle 37 and cover torque knobs 36. A battery compartment cover 31 is also provided. The patient breathing circuit being monitored is tapped into at an appropriate port or fitting using a conduit or a tube which has the other end secured to pressure inlet port fitting 34 on the back of the apparatus. Gas pressure tubing connected to port fitting 34 exposes the pressure to pressure switches which are described hereinafter.

Figure 3:
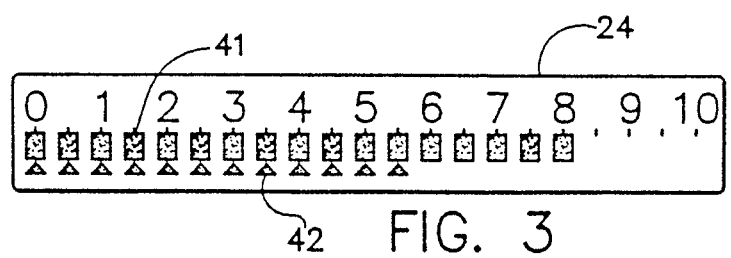
FIG. 3 is an enlarged representation of the visual display component on the apparatus.

In FIG. 3, the enlarged LCD visual manometer graph display is shown. Each bar 41 represents 0.5 cm H$_2$O, and each whole cm pressure is represented by the bars with the indicated numbers. The scale represented by the numbers on the bar graph are only representative of the type of unit and respiratory circuit to be monitored. For example, if an infant ventilator or C.P.A.P. circuit is monitored, a pressure range between 0 and 10 cm water as shown is suitable. For an adult model, pressures between 0 and 100 may be used, with the bar graph numbers for example each representing 10 cm water. The low pressure threshold which may be selected by the operator is also visible on the bar graph by the small triangles. Each triangle 42 represents a 0.5 cm water pressure. The display shown indicates the low pressure threshold being set at 5.5 cm water. Once that low pressure threshold is set, the display of triangles from left to right to the selected minimum set point remain visible on the display panel as long as the apparatus is turned on. If a higher pressure is set, additional triangles appear to so indicate the threshold pressure, and similarly, where a lower pressure is set, only the triangles appear up to the point. During patient breathing, with the unit turned on, the patient breathing cycle is indicated by the manometer pressure display bars 41 which appear and disappear with each breath of the patient. As a patient exhales, the exhalation pressure in the circuit being monitored causes display of that exhalation pressure by the bars which appear on the LCD display. Upon patient inhalation, with the pressure being sensed in the circuit falling to the lowest pressure, the bars disappear to the lowest pressure level sensed. Thus, an operator is able to observe the patient's breathing cycle by the bars repeatedly appearing and disappearing on the graph. In FIG. 3, display bars indicating patient breathing pressure at 8 cm $H_2O$ are shown by way of example. Any drift in the zero pressure point indicated on the bar graph may be corrected by adjusting offset adjustment screw 35 on the back cover.

Referring again FIG. 1, the operator may set up the unit by selecting both the low pressure minimum threshold using knob 14 and low pressure time delay by setting knob 13. This will be repeated with the high pressure threshold and time delay knobs 15 and 16. To activate the display, the unit may be first turned on manually using on off switch 11 which will activate the LCD visual display components. Alternatively, the unit will be turned on automatically by sensed pressure in the breathing circuit to which it is attached. Again, the adjustment of the low pressure threshold is then visually indicated on the display 24 by triangles 42. Of course, other visual indicators may be used, and those disclosed herein are for the purpose of illustration only and not to be considered to be limiting in any way of the type of visual symbols or display features which may be used.

Additional components illustrated in FIG. 1 include a high pressure LED 25 which will flash when the pressure rises above the selected high pressure threshold, and a low pressure LED 23 which flashes if the pressure fails to rise above and drop below the low pressure threshold for a period of time greater than the time delay selected by adjustment knob 13. Breath indicator 21 flashes whenever the pressure ascends through the low pressure threshold, and may also be programmed to flash when the unit is turned on or off. A low battery indicator LED 22 flashes when the remaining battery life is at a preselected minimum, which may also be programmed into the apparatus. Such a program is disclosed in U.S. Pat. No. 4,839,597, the description of which is incorporated herein by reference. A number of features including the automatic on component of the apparatus as well as the preselected minimum threshold pressure may incorporate components descried in U.S. Pat. No. 4,803,471, and where appropriate, those components including the electronics and descriptions thereof are incorporated herein by reference.

Figure 4:
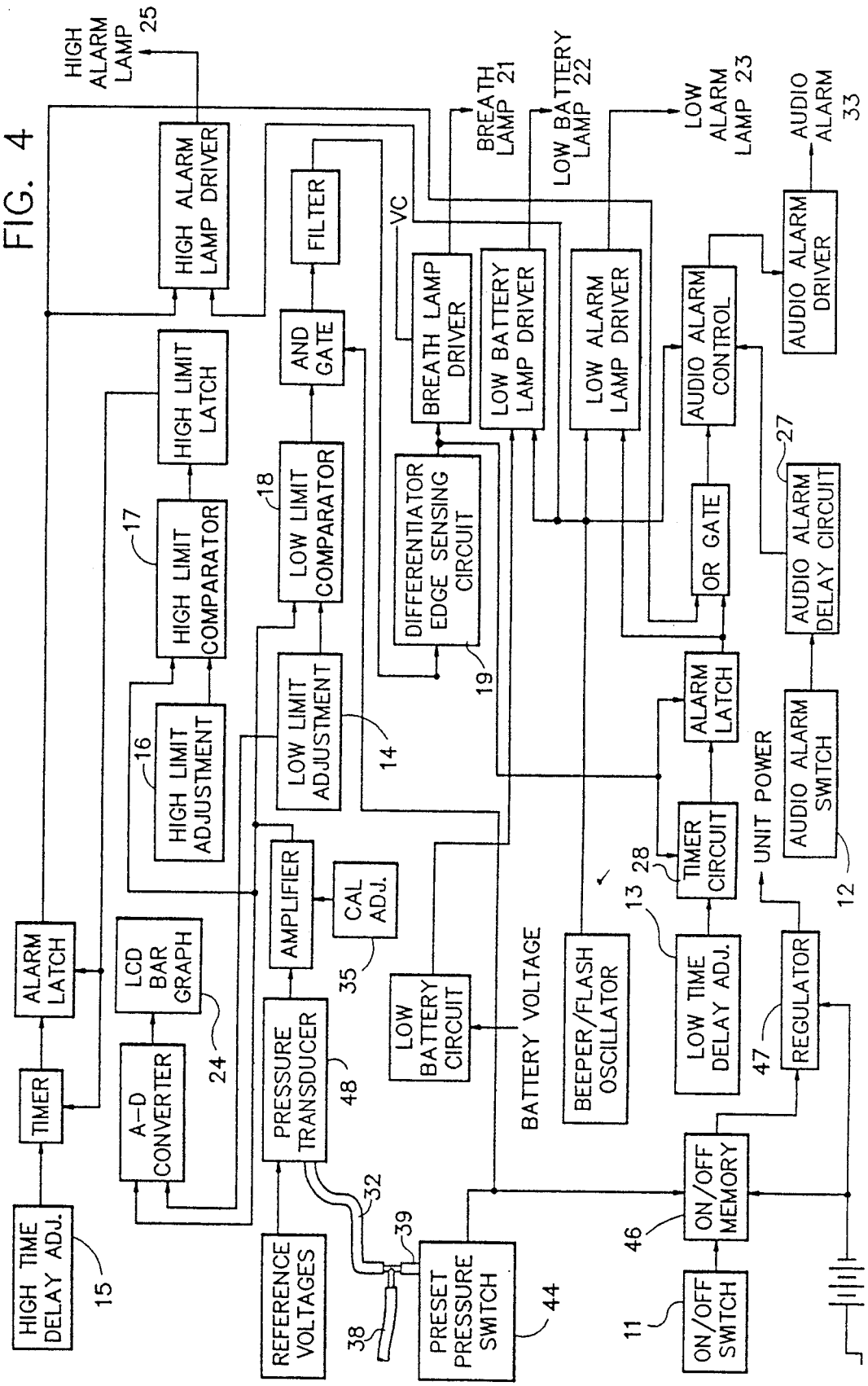
FIG. 4 is a block diagram illustrating the components of a preferred embodiment of the invention.
Figure 5:
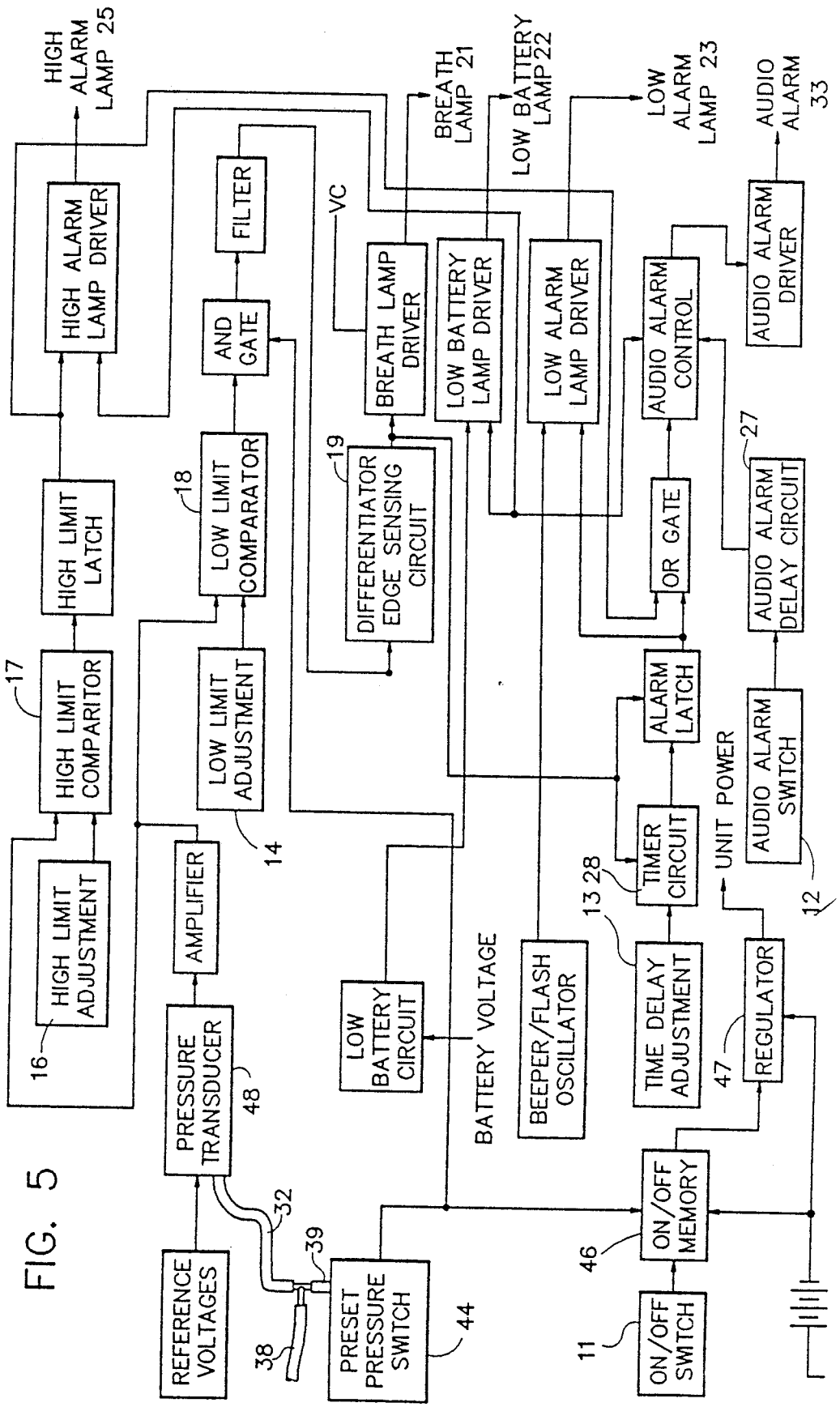
FIG. 5 is a block diagram of a more simplified embodiment of the invention.

In FIGS. 4 and 5, a number of the corresponding components illustrated in FIGS. 1-3 are identified. A significant improvement of the apparatus of the present invention over prior art devices is the use of two independent pressure sensing devices. A first pressure sensing means includes a preset pressure switch 44 for sensing the pressure in the respiratory circuit and automatically turning the unit on in response to the sensed pressure. Preferably, switch 44 is a mechanical switch which is preset to any desirable preset pressure, such as 2 cm water in the unit illustrated. This preset pressure switch also functions to create an alarm where the pressure drops below the preset pressure, in this case 2 cm water, for a time greater than the time delay period set by low pressure time delay adjustment knob 13. The alarm created by this feature and the functioning of the preset pressure switch 44 with the alarm enabling components will cause an alarm to occur regardless and independent of the adjustable low pressure threshold limit setting. It will be observed that the pressure switch 44 is electrically connected to the on/off memory component which comprises a logic circuit 46 and regulator 47. Again, the preset pressure switch 44 allows the apparatus to be turned on automatically and independently of the condition of on/off switch 11. The on/oft switch 11 and on/off memory logic circuit 46 is substantially as described in the aforesaid U.S. Pat. No. 4,803,471, and is incorporated herein by reference. The on/off switch preferably includes a delay switch to require the switch to be engaged for a preset period to avoid accidental engagement and turn off.

The breathing cycle pressure of the patient is monitored by electronic pressure transducer 48. The output of this pressure transducer is also preferably adjusted and calibrated to temperature differentials using a calibration adjustment component 35 connected to the amplifier as illustrated in FIG. 4 in the preferred embodiment. The pressure transducer actuates the LCD manometer bar graph 24 via A-D converter also illustrated in FIG. 4. The airway pressure in the ventilator circuit being monitored is exposed to pressure switch 44 and pressure transducer 48 via tubing components 38, 39 and 32. Inlet tube 38 is connected to pressure inlet port 34 on the back panel. A gas pressure tube (not shown) is secured between port 34 and the ventilator circuit.

Figures 1, 6:
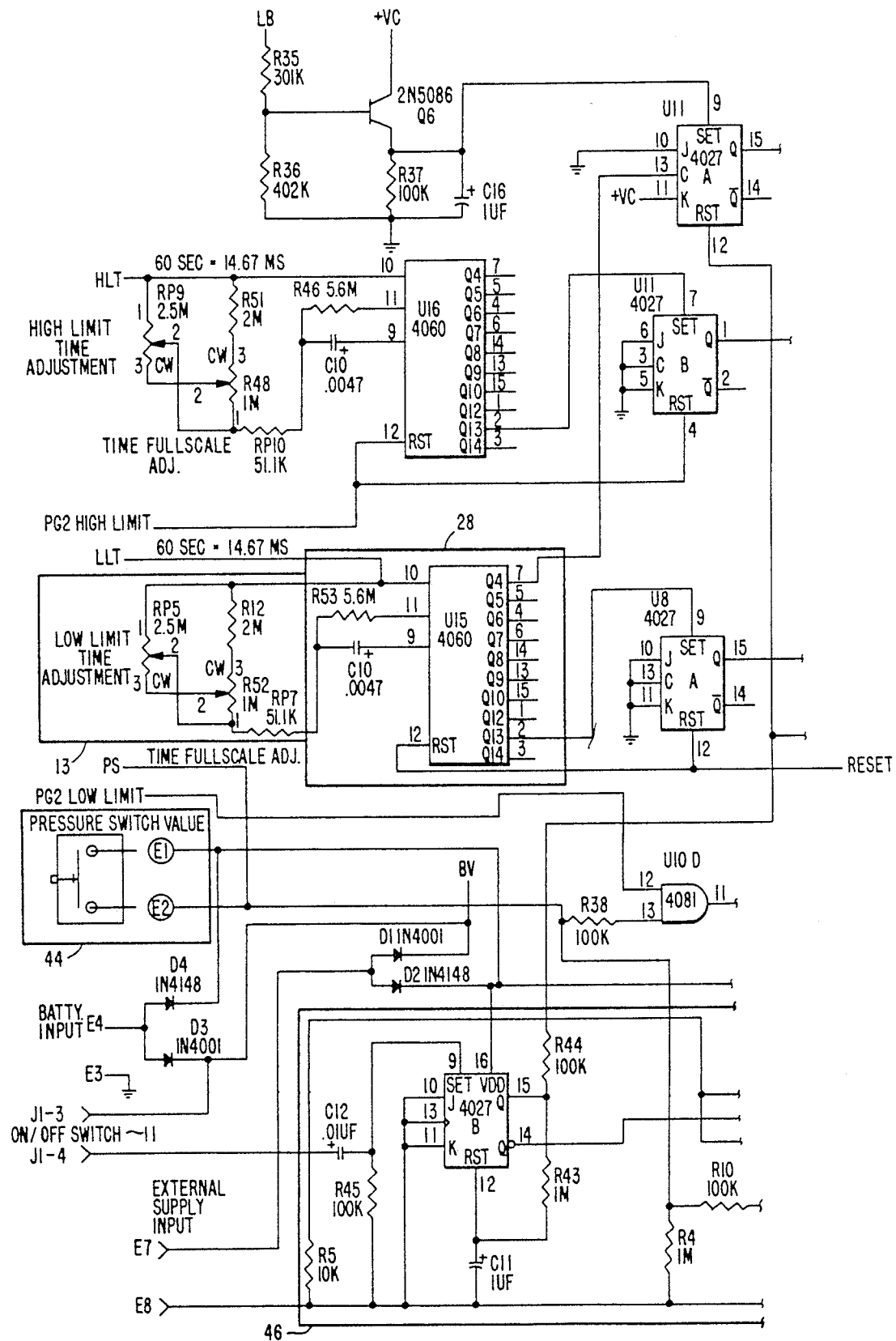
Figures 2, 6:
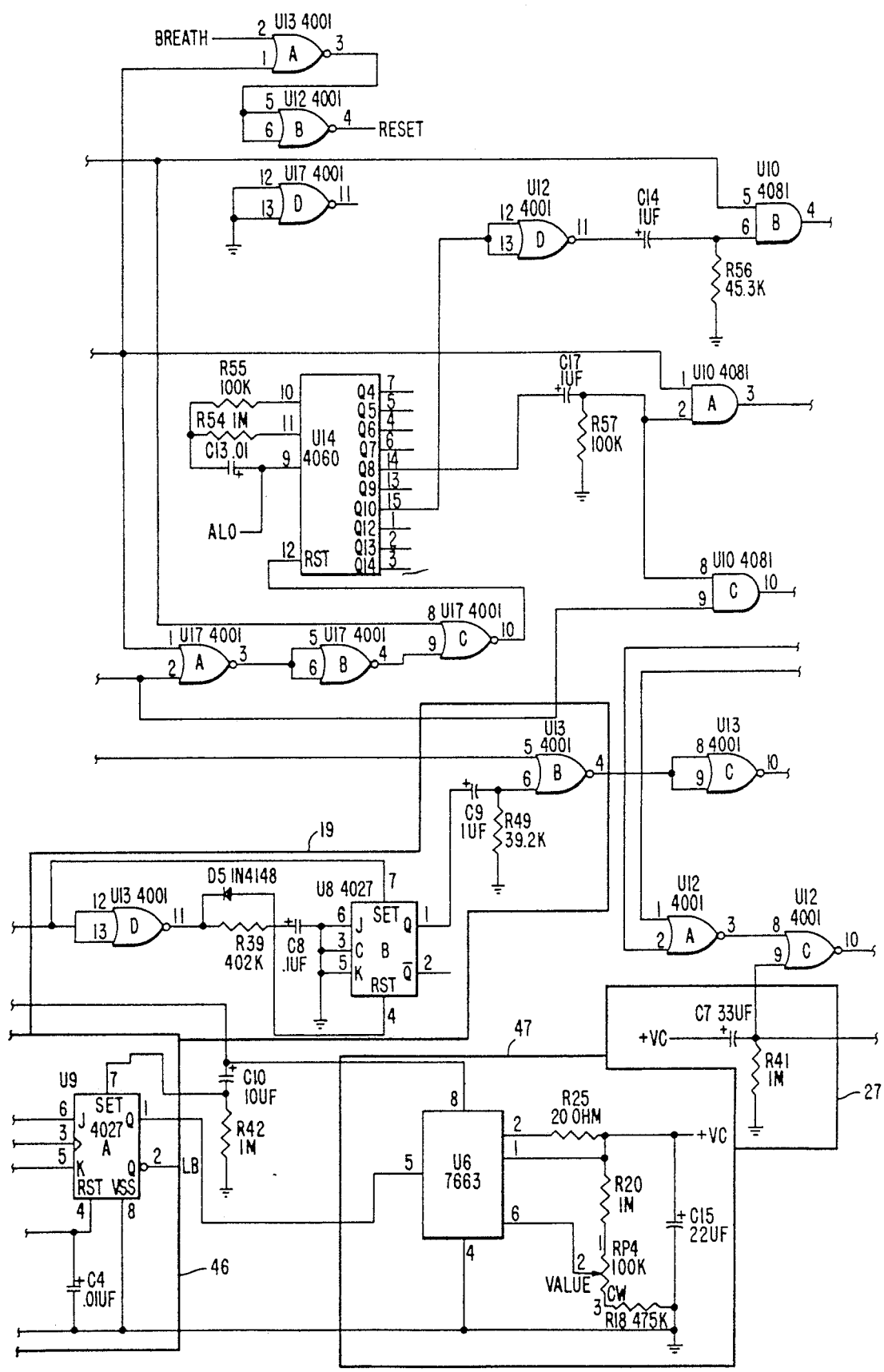
Figures 3, 6:
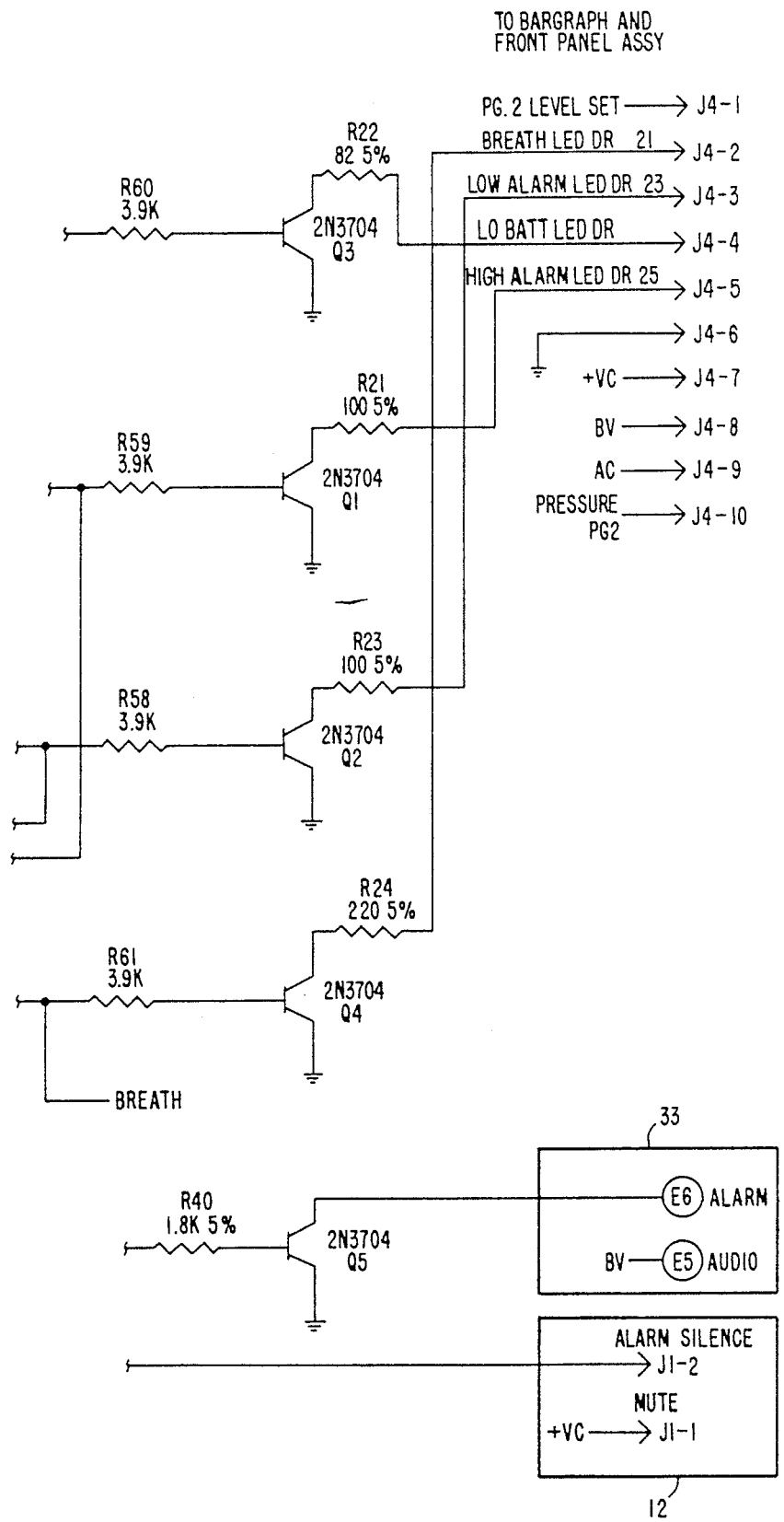
Figure 7:
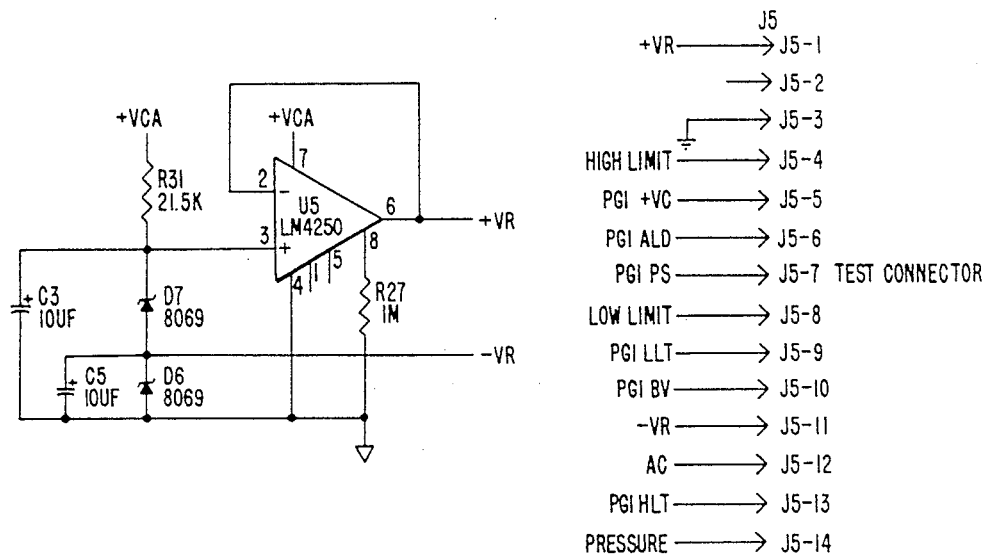
Figure 2:
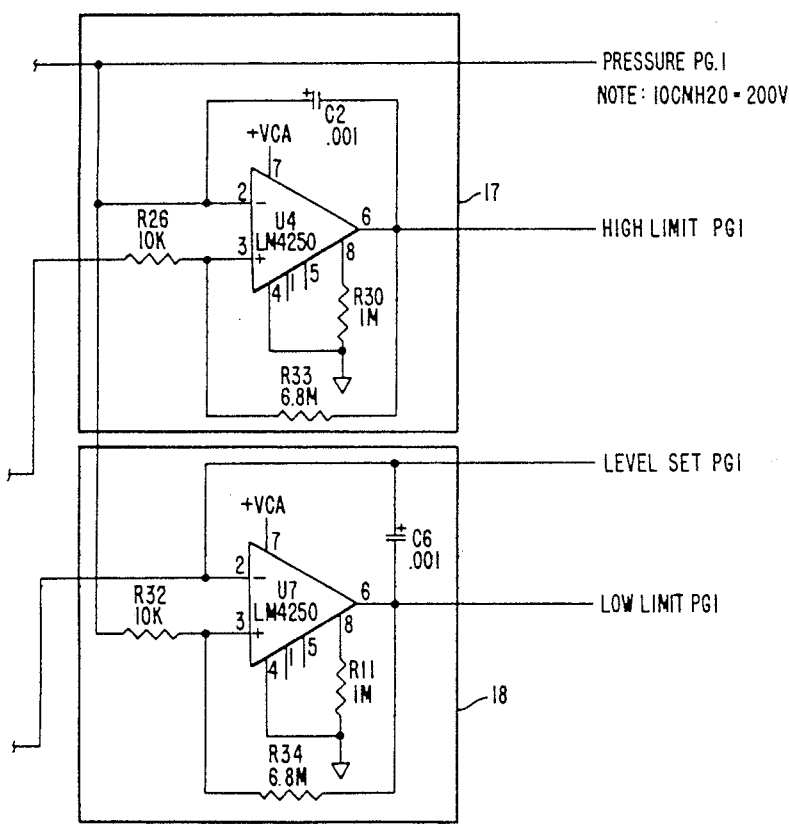
Figures 1, 7:
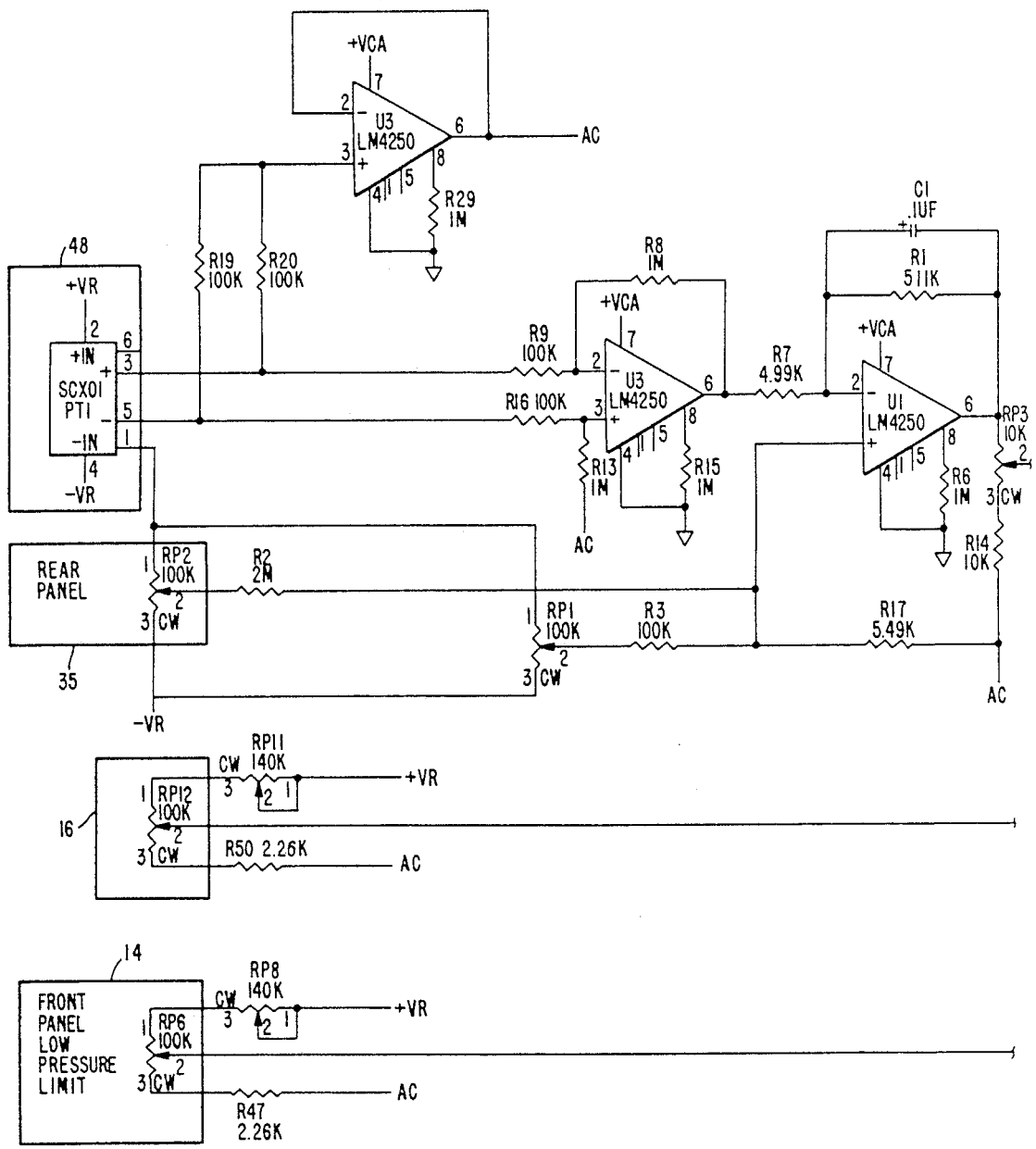

Other electronic components illustrated in FIGS. 4 and 5 include the low limit comparator and high limit comparator circuits 18 and 17, respectively, which compare the voltages from the pressure transducer with the respective low and high limit adjustment components 14 and 16. The low pressure alarm latch and high limit latch actuate the alarm circuits in response to the signals given from the comparators, respectively. Additionally, the differentiating edge sensing circuit component eliminates noise as well as filtering out unwanted spikes in the breathing signal received from the pressure transducer. These components as well as the others which are not specifically described other than named in the block diagram are also shown in FIGS. 6 and 7 with corresponding component numerals identifying the circuits. The structure and functioning of these components will be evident to those skilled in the art from the schematic and components shown.

The combination of components and resulting functioning of the device of the invention offer significant improvements over prior art devices such as previously described. The apparatus is turned on automatically by sensing the pressure in a respiratory circuit or patient airway, and the low pressure threshold is selected and monitored independent of the automatic on or pressure feature. The two independent pressure switches allow the operator or therapist to select a low threshold pressure at a level that is desirable for monitoring an individual patient without affecting the low pressure alarm that will occur anytime the pressure is below 2 cm $H_2O$ for the delay time period. Since the low pressure threshold can be selected at any desirable pressure, the unit operates to monitor the patient's breathing cycle without effecting the alarm capability of the apparatus to signal if the pressure falls below the preset pressure sensing switch 44. The high pressure sensing feature can be provided to operate with either a time delay, or with an instant alarm if the high pressure threshold is sensed. A remote unit electrically connected to the apparatus for monitoring desirable pressure and respiratory functions at a location some distance from the patient may also be provided. These advantages as well as others utilizing apparatus of the invention will be evident as will modifications within the purview of the invention.

We claim:

1. A monitor and alarm apparatus for monitoring a respiratory circuit comprising:
   (a) first pressure sensing means for sensing pressure in said respiratory circuit, and electronic circuit means cooperating therewith for turning said apparatus on in response to pressure sensed by said first pressure sensing means,
   (b) second pressure sensing means for continuously sensing the breathing cycle pressure of a user in said circuit independent of said first pressure sensing means,
   (c) first alarm enabling means for creating an alarm condition in response to pressure sensed by said first pressure sensing means being below a selected low pressure limit for a preselected period of time,
   (d) second alarm enabling means including adjustable low pressure threshold setting means for creating an alarm condition in response to said breathing cycle pressure sensed by said second pressure sensing means failing to pass through said low pressure threshold within a preselected period of time, and
   (e) alarm means actuated by said first and second alarm enabling means.

2. Apparatus of claim 1 including adjustable timing means for selecting said preselected period of time.

3. Apparatus of claim 1 including manual on-off switching means for turning the apparatus on and off, independent of said electronic circuit means.

4. Apparatus of claim 3 wherein said electronic circuit means includes memory circuit means for maintaining said apparatus turned on until said manual on/off switching means is actuated to turn said apparatus off.

5. Apparatus of claim 4 wherein said memory circuit comprises a digital logic circuit cooperating with said first pressure sensing means.

6. Apparatus of claim 1 including a third alarm enabling means and adjustable high pressure threshold setting means for creating an alarm condition in response to said breathing cycle pressure sensed by said second pressure sensing means exceeding said high pressure threshold pressure.

7. Apparatus of claim 1 wherein said first pressure sensing means comprises a pressure switch having preset pressure threshold for signaling said electronic circuit means for turning said apparatus on when pressure in said respiratory circuit reaches said preset pressure threshold.

8. Apparatus of claim 7 wherein said pressure switch comprises a mechanical pressure switch.

9. Apparatus of claim 7 wherein said pressure switch comprises a pressure transducer.

10. Apparatus of claim 1 wherein said adjustable low pressure threshold setting means comprises a pressure transducer.

11. Apparatus of claim 6 wherein said adjustable high pressure threshold setting means comprises a pressure transducer.

12. Apparatus of claim 1 including visual pressure indicating means comprising a pressure scale covering at least the normal pressure range of a patient's breathing cycle, a low pressure limit indicator cooperating with said adjustable low pressure threshold setting means for visually indicating the selected low pressure threshold pressure on said pressure scale, and a visual pressure indicator for graphically displaying the pressure of the patient's breathing cycle pressure on said pressure scale.

13. Apparatus of claim 12 wherein said pressure scale comprises a linear bar graph.

14. A monitor and alarm assembly for monitoring a respiratory circuit comprising:
   first pressure sensing means for sensing pressure in said respiratory circuit and first alarm enabling means cooperating therewith for creating an alarm condition in response to pressure sensed thereby being below a preselected minimum pressure sensed by said first pressure sensing means,
   second pressure sensing means for continuously sensing user breathing cycle pressure in said respiratory circuit and second alarm enabling means cooperating therewith including adjustable low pressure threshold setting means for creating an alarm condition in response to said breathing cycle pressure failing to pass through said low pressure threshold within a preselected time period, and
   alarm means actuated by either said first or second alarm enabling means.

15. A monitor of claim 14 wherein including a first timer means cooperating with said first alarm enabling means for creating said alarm condition after a preselected period of time.

16. A monitor of claim 14 wherein said first pressure sensing means comprises a mechanical pressure switch.

17. Apparatus of claim 3 wherein said manual on/off switching means comprises a switch having delay means whereby said switch must be engaged for a preselected minimum period of time to activate said switching means.

18. A monitor of claim 14 including manual on/off switching means for turning the monitor on and off, independent of said electronic circuit means.

19. A monitor and alarm assembly for monitoring a respiratory circuit comprising:
   first pressure sensing means for sensing pressure in said respiratory circuit and first alarm enabling means cooperating therewith for creating an alarm condition in response to pressure sensed thereby being below a preselected minimum pressure sensed by said first pressure sensing means,
   second pressure sensing means for continuously sensing user breathing cycle pressure in said respiratory circuit and second alarm enabling means cooperating therewith including adjustable low pressure threshold setting means for creating an alarm condition in response to said breathing cycle pressure failing to pass through said low pressure threshold within a preselected time period,
   alarm means actuated by either said first or second alarm enabling means, and
   visual pressure indicating means comprising a pressure scale covering at least the normal pressure range of a patient's breathing cycle, a low pressure limit indicator cooperating with said adjustable low pressure threshold setting means for visually indicating the selected low pressure threshold pressure on said pressure scale, and a visual pressure indicator for graphically displaying the pressure of the patient's breathing cycle pressure on said pressure scale.

* * * * *